Figure 1:
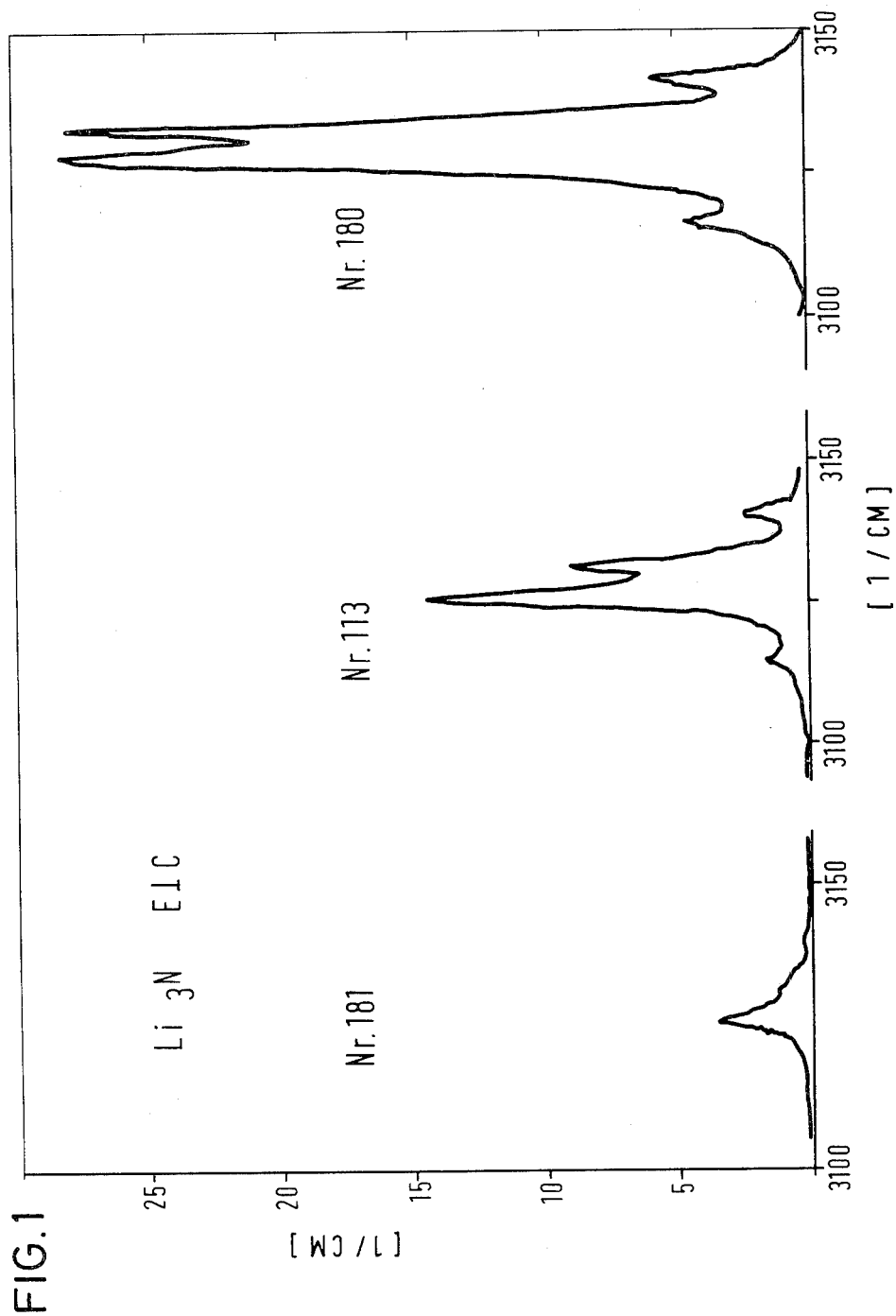

United States Patent [19]

Wahl et al.

[11] 4,321,163

[45] Mar. 23, 1982

[54] LITHIUM NITRIDE OF INCREASED CONDUCTIVITY, METHOD FOR ITS PREPARATION, AND ITS USE

[75] Inventors: Jochen Wahl, Immenstaad; Alfred Breitschwerdt, Stuttgart, both of Fed. Rep. of Germany

[73] Assignee: Max-Planck-Gesellschaft, Gottingen, Fed. Rep. of Germany

[21] Appl. No.: 95,714

[22] Filed: Nov. 19, 1979

[30] Foreign Application Priority Data

Nov. 21, 1978 [DE] Fed. Rep. of Germany ....... 2850460

[51] Int. Cl.³ ............................................... H01B 1/06
[52] U.S. Cl. .................................... 252/518; 252/512; 252/513; 252/514; 252/515; 252/521; 252/182.1; 423/406; 423/407; 423/409; 429/218
[58] Field of Search ............... 423/406, 409, 407, 413; 252/518, 500, 512, 514, 515, 513, 521, 182.1; 429/218

[56] References Cited

U.S. PATENT DOCUMENTS

| | | | |
|---|---|---|---|
| 2,866,685 | 12/1958 | Lam et al. | 423/409 |
| 2,910,347 | 10/1959 | Esmay | 423/409 |
| 3,542,512 | 11/1970 | Honeycutt | 423/413 |
| 4,169,808 | 10/1979 | Klemann et al. | 252/518 |
| 4,196,178 | 4/1980 | Iwai et al. | 423/406 |
| 4,206,191 | 6/1980 | Morrison et al. | 423/413 |

*Primary Examiner*—J. L. Barr

[57] ABSTRACT

Crystalline lithium nitride of increased conductivity having a hydrogen content of 0.2 to about 8 mole percent, a sodium, potassium and calcium content each of less than $10^{-2}$ weight percent and a silicon and iron content each between $10^{-2}$ to $10^{-3}$ weight percent, the metallic lithium from which said crystalline lithium was prepared having been of at least 99.9 weight percent purity.

11 Claims, 2 Drawing Figures

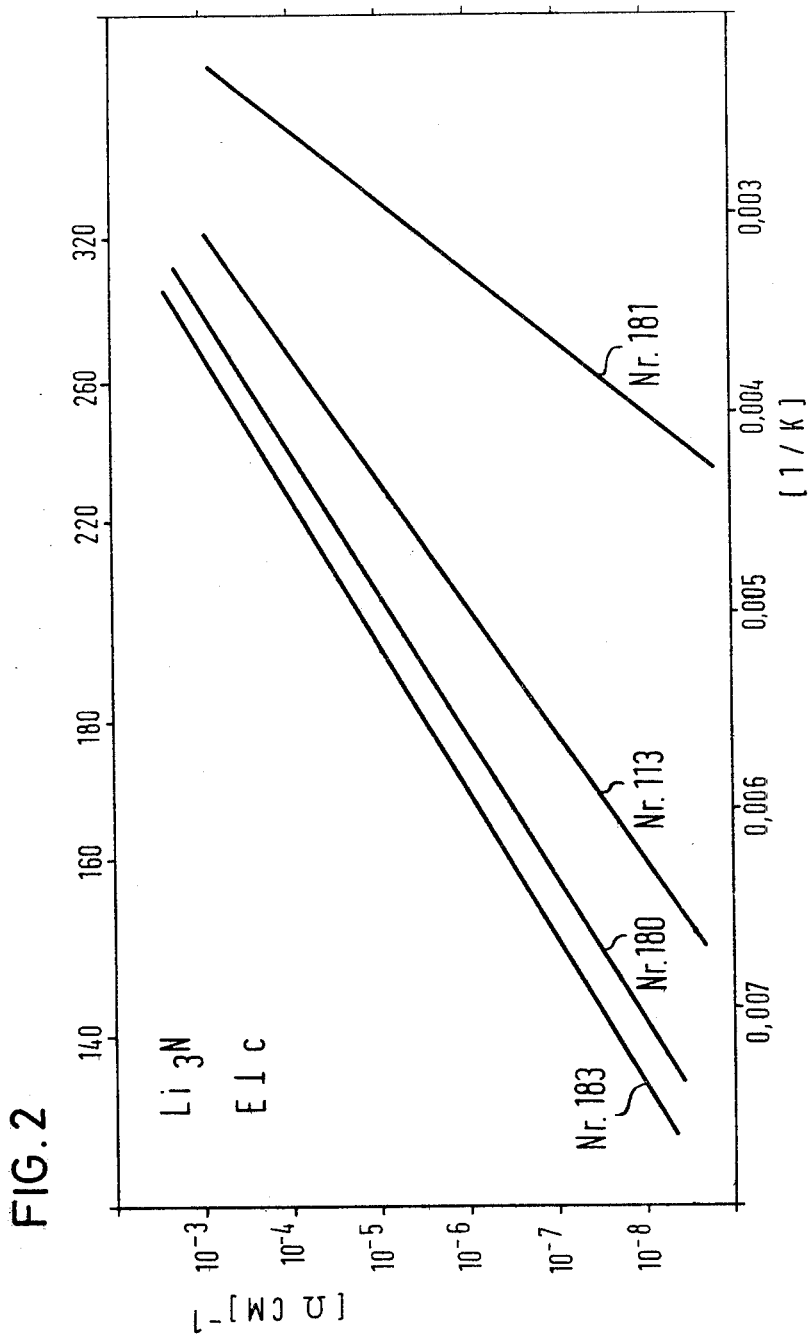

LITHIUM NITRIDE OF INCREASED CONDUCTIVITY, METHOD FOR ITS PREPARATION, AND ITS USE

The invention relates to a crystalline lithium nitride of increased conductivity, a method for its production, and its use.

On account of its strong electropositive character and its low equivalent weight, lithium in the form of its compounds is of particular interest for solid, ion-conducting electrolytes. Lithium nitride possesses particularly good characteristics as regards ionic conductivity.

However, its stability and ionic conductivity are less than satisfactory. It would be very desirable to improve these or make them controllable. It has now been found, and on this the invention is based, that it is possible to increase this ionic conductivity and to regulate it by doping the lithium nitride with hydrogen.

In accordance with the invention, therefore, a crystalline lithium nitride of improved and/or regulated conductivity is characterized by a content of hydrogen. Within the scope of the invention, the term hydrogen is intended to include hydrogen itself as well as its isotopes, deuterium and tritium.

In the hydrogen-doped lithium nitride of the invention, $N^{3-}$ sites are formed in the $Li_3N$ lattice by nitrogen-hydrogen complex compounds, particularly $(NH)^{2-}$ and $(NH_1)^{1-}$, so that lithium vacancies are formed for charge compensation. The ionic conduction is improved by these lithium vacancies.

Especially high conductivities are obtained with hydrogen contents of approximately 0.2 to about 8 mole percent with respect to the nitrogen content of the lithium nitride. This means that 0.2 to 8 mole percent of the nitrogen which is bound in the lithium nitride lattice is replaced by a nitrogen-hydrogen complex compound.

Particularly good results have been obtained with a hydrogen content of 2 to 6 mole percent, and the best results have been obtained at approximately 3 to 5 mole percent.

The lithium nitride crystals doped with hydrogen in accordance with the invention have a certain conductivity according to the hydrogen content, which is as much as 5000 times greater at the same temperature than the conductivity of a corresponding hydrogen-free lithium nitride. It is especially important that these conductivity differences are even more pronounced at lower temperatures, so that especially the ion conductivity at room temperature and lower temperatures is increased to an especially great degree. Furthermore, it is important that specific conductivities can now be obtained in a repeatable manner.

In order to improve stability in air, the following purity standards are maintained in the crystalline lithium nitride of the invention.

A Na content of less than $10^{-2}$ wt.-%, a K and Ca content of less than $10^{-2}$ wt.-% each, an Mg content under $1 \times 10^{-2}$ wt.-%, and an Si and Fe content of $10^{-2}$ to $10^{-3}$ wt.-% each, and it must have been prepared from a metallic lithium of at least 99.9 wt.-% purity in an inert vessel. Inert vessel materials are especially tungsten, niobium, ruthenium and tantalum. Tungsten is particularly preferred.

The production of the lithium nitride of the invention is accomplished in principle by the reaction of lithium and nitrogen in the presence of hydrogen. The hydrogen can be in the form of molecular hydrogen or in the form of a compound with the two reaction components, especially in the form of ammonia or lithium hydride. However, other nitrogen-hydrogen compounds such as hydrazine can also be used. The production is best accomplished either by heating at least 99.9% pure lithium metal at 140° to 180° C. in a tungsten crucible at a nitrogen pressure of at least 250 mm Hg and increasing the temperature to 400° to 600° C. to the melting point of $Li_3N$, or by reacting it at a nitrogen pressure less than atmospheric, but above 250 mm Hg, at a temperature above 300° C. In accordance with the invention, this is modified by operating in the presence of hydrogen or of a compound of hydrogen with one of the reaction components.

The hydrogen addition is performed in a molar amount which results in the desired doping. In general nitrogen-hydrogen mixtures are used which contain approximately 0.1 to 10 mole percent of hydrogen. As mentioned above, instead of ordinary hydrogen, a hydrogen isotope or a mixture of hydrogen isotopes can be used. The hydrogen content of the crystalline lithium nitride does depend on the amount of bound or free hydrogen added in the preparation of the lithium nitride and on the conditions of the process, but is not proportional. The best doping rates have been achieved when the reaction was performed at temperatures which were not above 500° C.

Hydrogenated lithium nitride prepared in the manner described above can then be recrystallized near the melting point of lithium nitride, i.e., up to about 840° to 850° C., with the formation of large monocrystals. The process known as the Czochralski process, as described, for example, in Journal of Crystal Growth 43 (1978) 469, has proven especially effective. For practical applications, however, the finely crystalline powder, such as is easily obtained without further recrystallization, is suitable. It can be pressed into compacts as desired and then can be sintered. Sintering under high pressure, e.g., 1 to 3 kbar, at 600° to 700° C. in a nitrogen atmosphere, has proven especially effective.

The relative hydrogen content of the hydrogenous crystalline lithium nitride of the invention can be determined by measuring the infrared transmission. The valance vibration of the N—H bond is at 3125 cm$^{-1}$, and the valence vibration of the N—D bond is at 2320 cm$^{-1}$. Since absorption is observed only perpendicularly to the hexagonal axis of the crystal, it can be concluded that the N—H axis is oriented perpendicular to the hexagonal axis. Since the integral over the absorption coefficients is proportional to the hydrogen concentration, the relative hydrogen content can be determined in this manner.

In the appended drawing,

FIG. 1 is a graphic representation of the infrared absorption coefficients for three different crystals of the invention as a function of the wave number, FIG. 2 is a graphic representation of the ionic conductivity of four crystals of the invention having different hydrogen contents.

FIG. 1 shows, as stated, the absorption coefficients for three hydrogen-doped lithium nitride crystals as a function of the wave number for an electrical field perpendicular to the hexagonal axis. An absorption is observed only at this orientation of the field. The integral over the absorption coefficients is proportional to the hydrogen content. The determination was performed at 77 K.

In FIG. 2, the ion conductivity of four hydrogen-doped lithium nitride crystals is represented as a function of the inverse temperature. Three of these four crystals are identical with the crystals on which FIG. 1 is based. Crystal No. 181 has the lowest hydrogen content (about 0.3 mole percent), crystal No. 180 the highest content (about 5 mole percent). In the case of crystals No. 113 and No. 183, the hydrogen content amounts to approximately 2 and 4 mole percent, respectively. The analytic values for the individual crystals are given in the following table, which shows the conductivity $\sigma$ of lithium nitride monocrystals of various hydrogen content. The integral I over the absorption coefficients $\alpha$ (in the area of the valence vibration at 3125 cm$^{-1}$) is proportional to the hydrogen content. The conductivities at 300 K are also given. The crystal orientation corresponds to the direction of highest conductivity.

TABLE

| Sample No. | $I = \int \alpha(\kappa)d$ | $\sigma(T)$ $(\Omega\,cm)^{-1}$ | $\sigma(T = 300\,K)$ $(\Omega cm)^{-1}$ |
|---|---|---|---|
| 181 | 24 | 2000 exp (−6500/T) | $6 \times 10^{-7}$ |
| 113 | 140 | 60 exp (−3600/T) | $3.5 \times 10^{-4}$ |
| 183 | 311 | 90 exp (−3100/T) | $3 \times 10^{-3}$ |
| 180 | 360 | 70 exp (−3200/T) | $1.5 \times 10^{-3}$ |

The table shows a drastic increase in the ion conduction as the hydrogen content increases. From the material of the lowest hydrogen content, crystal No. 181, to the crystal with the highest conductivity (No. 183) there is a variation by a factor of 5000 at 300 K. At low temperatures these differences are still greater.

It is remarkable that in the crystal with the highest hydrogen content (No. 180) the conductivity decreases again slightly; in other words, here the optimum has been passed.

On the basis of an X-ray structural test it was found that there was a concentration of approximately 1% lithium vacancies in the Li$_2$N$_2$ layers also in crystal No. 113. In the defective model containing (NH)$^{2-}$ and (NH$_2$)$^{1-}$ impurities, each hydrogen atom produces a lithium vacancy for charge compensation. The number of hydrogen atoms can then be inferred from the number of vacancies. For No. 113 it is found that 2 mole percent of nitrogen is substituted by NH. With the integrals in the table one obtains the absolute values for the other crystals.

The following example will further explain the manufacture of the doped lithium nitride crystals of the invention.

EXAMPLE

Approximately 100 grams of lithium metal were melted in vacuo in a tungsten crucible in a fully enclosed apparatus. The molten lithium was kept in a vacuum of 10$^{-4}$ Torr for several hours at 300° C. to remove escaping gases. Then a nitrogen-hydrogen mixture with a content of 9 mole percent of hydrogen was introduced into the apparatus, while the lithium was held at a temperature of 500° C. The gas pressure was held at about 400 Torr until the end of the reaction, and was then set at 700 Torr until no further absorption of nitrogen could be detected.

From the crystalline mass thus obtained, monocrystals were then drawn at 840° C. by the method described in the Journal of Crystal Growth 43 (1978), 469, and these were used for the testing of the characteristics. The characteristics of the crystal obtained are shown in the Table (Crystal No. 183).

The above process was repeated with a hydrogen content of 10 mole percent in the nitrogen-hydrogen mixture. The temperature of the lithium metal in the reaction was 520° C. The properties of the crystals thus obtained are represented in the Table (No. 180).

A similar procedure was followed for the production of crystals Nos. 181 and 113 in the Table. However, in this case the molar hydrogen concentration in the mixture of reaction gases was 1 and 5 mole percent, respectively.

We claim:

1. Crystalline lithium nitride of increased conductivity comprising 0.2 to about 8 mole percent of hydrogen, a sodium, potassium, and calcium content each of less than 10$^{-2}$ weight percent and a silicon and iron content each between 10$^{-2}$ to 10$^{-3}$ weight percent, the metallic lithium from which said crystalline lithium nitride was prepared having been of at least 99.9 weight percent purity.

2. Crystalline lithium nitride of claim 1 wherein the hydrogen content is 2 to 6 mole percent.

3. Method of preparing crystalline lithium nitride of increased conductivity from lithium metal of at least 99.9 weight percent purity comprising the steps of heating the lithium metal to a temperature of 140° C. to 180° C. in an inert vessel in the presence of sufficient hydrogen for complete reaction with the lithium metal, at a nitrogen pressure of at least 250 mm Hg and, after the onset of the reaction, increasing the temperature to the melting point of lithium nitride; or heating said lithium metal in the presence of hydrogen at a nitrogen pressure of at least 250 mm Hg, but below atmospheric pressure to a temperature above 300° C., in said inert vessel, said inert vessel being formed of tungsten, niobium, ruthenium or tantalum; said hydrogen being present in an amount in excess of 0.2 to about 8 moles, per mole of lithium nitride.

4. Method of claim 3 wherein hydrogen is present in the form of ammonia.

5. Method of claim 3 wherein hydrogen is present in the form of lithium hydride.

6. Method of claim 3 wherein the hydrogen is present in an amount of 1 to 10 mole percent with respect to the nitrogen.

7. Method of claim 3 wherein the crystals obtained are recrystallized in a nitrogen atmosphere at a temperature of 840° to 850° C.

8. Method of claim 3 wherein said hydrogen is in the form of hydrogen gas mixed with the nitrogen in an amount of about 9 mole percent hydrogen, the lithium nitride being held at 400 torr until the end of the reaction, and thereafter raised to 700 torr until no further absorption of nitrogen could be detected.

9. Use of the crystalline lithium nitride of claim 1 as an ion conductor in a lithium cell, a nitrogen sensor or a display screen.

10. In a method of regulating the conductivity of crystalline lithium nitride which is obtained by the reaction of metalic lithium with nitrogen at a temperature of about 140° to 180° C. in an inert vessel the steps comprising adding, to the reaction, hydrogen in molecular form or in the form of a compound with one of the two reactants, in such an amount that a hydrogen content corresponding to the desired conductivity and in the range of 0.2 to 8 mole percent is put in a dopant.

11. Method of claim 10, characterized in that 0.2 to 8 mole percent of hydrogen is incorporated into the crystal.

* * * * *